United States Patent
Yasuda et al.

(10) Patent No.: US 6,777,531 B2
(45) Date of Patent: Aug. 17, 2004

(54) END-CAPPED POLYFLUORENES, FILMS AND DEVICES BASED THEREON

(75) Inventors: Akio Yasuda, Stuttgart (DE); Wolfgang Knoll, Mainz (DE); Andreas Meisel, Frankfurt am Main (DE); Tzenka Miteva, Stuttgart (DE); Dieter Meher, Potsdam (DE); Heinz-Georg Nothofer, Stuttgart (DE); Ullrich Scherf, Golm (DE)

(73) Assignees: Sony International (Europe) GmbH, Berlin (DE); Max-Plack-Gesellschaft zur Forderung der Wissenschaften, E.V., Munich (DE)

(*) Notice: Subject to any disclaimer, the term of this patent is extended or adjusted under 35 U.S.C. 154(b) by 0 days.

(21) Appl. No.: 10/019,208

(22) PCT Filed: Apr. 20, 2001

(86) PCT No.: PCT/EP01/04522

§ 371 (c)(1),
(2), (4) Date: May 2, 2002

(87) PCT Pub. No.: WO01/81294

PCT Pub. Date: Nov. 1, 2001

(65) Prior Publication Data

US 2002/0173617 A1 Nov. 21, 2002

(30) Foreign Application Priority Data

Apr. 26, 2000 (EP) .............................. 00108877

(51) Int. Cl.⁷ ............................... C08G 73/00

(52) U.S. Cl. ................. 528/422; 528/423; 528/425; 528/373; 428/690; 428/917; 428/433.1

(58) Field of Search .................. 528/422, 423, 528/425, 373; 428/690, 917, 423.1

(56) References Cited

FOREIGN PATENT DOCUMENTS

| WO | WO 97 05184 | 2/1997 |
| WO | WO 99 54385 | 10/1999 |

OTHER PUBLICATIONS

Nothofer et al "Liquid crystalline polyflurenes for blue polarized electroluminescence", 2000, Chem Abstract 133: 141917.*

Seda et al "Organic electronic device using charge transporting polyester", 1996, 125: 342810.*

Lee J–I et al: "Light–Emitting Electrochemical Cells Based on Poly(9,9–bis(3,6–dioxeheptyl)–fluorene–2,7–diyl)" 2nd International Conference on Elecroluminescence of Molecular Materials and Related Phenomena, Sheffield, UK, May 15–18, 1999, vol. 111–112, pp. 195–197, XP000951433.

Patent Abstracts of Japan, vol. 2000, No. 02, Feb. 29, 2000, JP 11 322679.

* cited by examiner

*Primary Examiner*—Duc Truong
(74) *Attorney, Agent, or Firm*—Frommer Lawrence & Haug LLP; William S. Frommer; Samuel H. Megerditchain

(57) ABSTRACT

The present invention relates to polyfluorenes end-capped with at least one charge-transporting moiety, and to films and devices based thereon.

28 Claims, 7 Drawing Sheets

END-CAPPED POLYFLUORENES, FILMS AND DEVICES BASED THEREON

The present invention relates to end-capped polyfluorenes, films and devices based thereon.

In recent years much attention has been paid to polymers being useful for incorporation into field-effect transistors, light-emitting diodes (LEDs) and photo-voltaic devices. A wide variety of polymers have been included as active media in these electronic devices. A class of compounds that has been found to be potentially useful for such purpose are the polyfluorenes.

Various reasons support the use of polyfluorenes in these devices: First of all, polyfluorenes are displaying impressive blue-emission properties and because of this they received considerable attention with respect to their potential for inclusion into emission layers of LEDs. Several reports have demonstrated bright blue emission from polyfluorene homopolymers (A. W. Grice; D. D. C. Bradley; M. T. Bernius; M. Inbasekaran; W. W. Wu; E. P. Woo; *Appl. Phys. Lett.* 1998, 73, 629; Y. Yang and Q. Pei; *J. Appl. Phys.* 81, 3294 (1997)).

A second important property of polyfluorenes, in particular polyfluorene homopolymers, is their thermotropic liquid-crystalline behaviour, which allows to orient these polymers on alignment layers, for example rubbed polyimide layers (M. Grell, D. D. C. Bradley, M. Inbasekaran, E. P. Woo, *Adv. Mater.* 9, 798 (1997); M. Grell, D. D. C. Bradley, X. Long, T. Chamberlain, M. Inbasekaran, E. P. Woo, M. Soliman, Acta Polym. 49, 439 (1998)). Orientation of the polymers on such alignment layers enables the emission of linearly polarized light which is particularly useful for devices such as liquid-crystal (LC) displays in which emission layers incorporating polyfluorene are being used as backlights. LEDs emitting linearly polarized light and having a dichroic ratio in emission of more than 20 and a brightness in excess of 100 cd/m² could be fabricated when the polyimide layers were doped with appropriate hole-transporting molecules (M. Grell, W. Knoll, D. Lupo, A. Meisel, T. Miteva, D. Neher, H. G. Nothofer, U. Scherf, H. Yasuda, Adv. Mater. 11, 671 (1999).

The efficiency of devices based on non-aligned and aligned polyfluorenes is, however, still far too low for applications. The efficiency of a bilayer device comprising a cross-linked hole-transporting layer (HTL) and an emission layer (EML) based on poly(9,9-bis(n-octyl)fluorene-2,7-diyl) (PFO) with linear octyl side-chains was only 0.25 cd/A (A. W. Grice; D. D. C. Bradley; M. T. Bernius; M. Inbasekaran; W. W. Wu; E. P. Woo; *Appl. Phys. Lett.* 73, 629 (1998)). Devices with aligned polyfluorenes, using poly(9,9-bis(2-ethylhexyl)fluorene-2,7-diyl) are reported to show an even lower efficiency of approximately 0.12 cd/A (M. Grell, W. Knoll, D. Lupo, A. Meisel, T. Miteva, D. Neher, H. G. Nothofer, U. Scherf, H. Yasuda, Adv. Mater. 11,671 (1999)).

Several attempts have been made to chemically modify polyfluorenes in order to increase the device efficiency. For example Kim et al. (Macromolecular Symposia, 1999, 143, 221–230) copolymerized 2,7-diethynyl-9,9'-di-n-hexylfluorene and 2,7-dibromo-9,9'-di-n-hexylfluorene to yield poly(9,9'-di-n-hexyl-2,7-fluorenyleneethynylene). The alternating copolymer emitted blue colour with a peak maximum at 475 nm on excitation either at 340, 365 or 400 mn. The principle emission maximum shifted to 425 nm on excitation at 340 nm when the polymer was blended with polyvinylcarbazole (PVK). Light-emitting diodes (LEDs) fabricated with the alternating copolymer sandwiched between indium-tin oxide glass and Al emitted a light with a peak maximum at 550 nm. The peak maximum shifted to 425 nm when the copolymer was blended with PVK with the blending ratios between 5 to 20% of the emissive copolymer.

Colour tuning was deliberately achieved via incorporation of benzothiadiazole, perylene or anthracene moieties (Klaerner, G.; Davey, M. H.; Chen, W. D.; Scott, J. C.; Miller, R. D.; *Adv. Mater.* 10, 993 (1998); M. Kreyenschmidt, G. Klärner, T. Fuhrer, J. Ashenhurst, S. Karg, W. D. Chen, V. Y. Lee, J. C. Scott, R. D. Miller, *Macromolecules* 31, 1099 (1998); Y. He, S. Gong, R. Hattori, J. Kanicki, *Appl. Phys. Lett.* 74, 2265 (1999)). The problem, however, with the inclusion of such chemical moieties into the polyfluorene main chain or the copolymerization with other monomers is the inevitable modification of essential properties of the main chain such as the stiffness and the geometrical shape, thereby inadvertently altering the character of the polyfluorene, e. g. its liquid-crystalline behaviour, if such had been present before any modification.

Another problem with LED-devices based on polyfluorene emission layers is that the emission spectrum of such an LED exhibits a significant contribution of longer wavelengths, particularly in the range of the red part of the spectrum (M. Grell, D. D. C. Bradley, X. Long, T. Chamberlain, M. Inbasekaran, B. P. Woo, M. Soliman; *Acta Polym.* 49, 439 (1998); M. Grell, W. Knoll, D. Lupo, A. Meisel, T. Miteva, D. Neher, H. G. Nothofer, U. Scherf, H. Yasuda, Adv. Mater. 11, 671 (1999); J. Teetsov, M. A. Fox; *Journal of Materials Chemistry* 9, 2117 (1999), V. N. Bliznyuk, S. A. Carter, J. C. Scott, G. Klärner, R. D. Miller, and D. C. Miller; *Macromolecules* 32, 361 (1999)). The strength of this contribution changes strongly with the molecular weight and the nature of the side chains. This situation is aggravated by the fact that the alignment of the polymer in the liquid-crystalline state requires an annealing step at higher temperatures enhancing this undesired red contribution. Several attempts have been made towards a control of red-shifted emission bands. These include the synthesis of statistical (M. Kreyenschmidt, G. Klärner, T. Fuhrer, J. Ashenhurst, S. Karg, W. D. Chen, V. Y. Lee, J. C. Scott, R. D. Miller; *Macromolecules* 1998, 31, 1099) or block (D. Marsitzky, M. Klapper, K. Müllen; *Macromolecules* 1999, 32, 8685) copolymers, the attachment of sterically demanding groups (G. Klärner, R. D. Miller, C. J. Hawker; *Polym. Prepr.* 1998, 1006) or thermal cross-linking of terminal reactive groups, e. g. benzocyclobutane ((a) E. P. Woo, M. Inbasekaran, W. Shiang, G. R. Roof; *Int. Pat. Appl.* WO97/05184 (1997); (b) M. Inbasekaran, W. Wu, E. P. Woo; U.S. Pat. No. 5,770,070 (1998)) units or unsaturated functions (e. g. styryl) (Klaerner, G.; Davey, M. H.; Chen, W. D.; Scott, J. C; Miller, R. D.; *Adv. Mater.* 1998, 10, 993; G. Klärner, J.-I. Lee, V. Y. Lee, E. Chan, J.-P. Chen, A. Nelson, D. Markiewitz, R. Siemens, J. C. Scott, R. D. Miller; *Chem. Mater.* 1999, 11, 1800). In most of these cases the electronic properties as well as the phase behaviour have become severely altered compared to that of the polyfluorene homopolymers. For example the synthesis of block copolymers has in fact led to an even increased contribution of undesired red-shifted emission states (D. Marsitzky, M. Klapper, K. Müllen; ibid.).

Accordingly, it is an object of the present invention to provide polymers useful for incorporation into electronic devices such as FETs, LEDs and photovoltaic devices which do not show any unwanted red-shift contribution. Particularly it is an object of the present invention to provide polyfluorenes useful for incorporation into these devices which do not show any undesired red-shift contribution. Another object of the present invention is to provide polymers, in particular polyfluorenes, that allow for the fabrication of electronic devices, in particular LEDs, FETs and photovoltaic devices with a higher efficiency. It is another object of the present invention to provide LEDs with a higher brightness, a lower onset voltage, a negligible red contribution, a better colour stability and the potential to achieve high dichroic ratios.

All these objects are solved by a polyfluorene end-capped with at least one charge-transporting moiety.

It is preferred that in such a polyfluorene the charge-transporting moiety is selected from the group comprising electron-transporting moieties, hole-transporting moieties and ion-transporting moieties, wherein, more preferably, the charge-transporting moiety is selected from the group comprising:

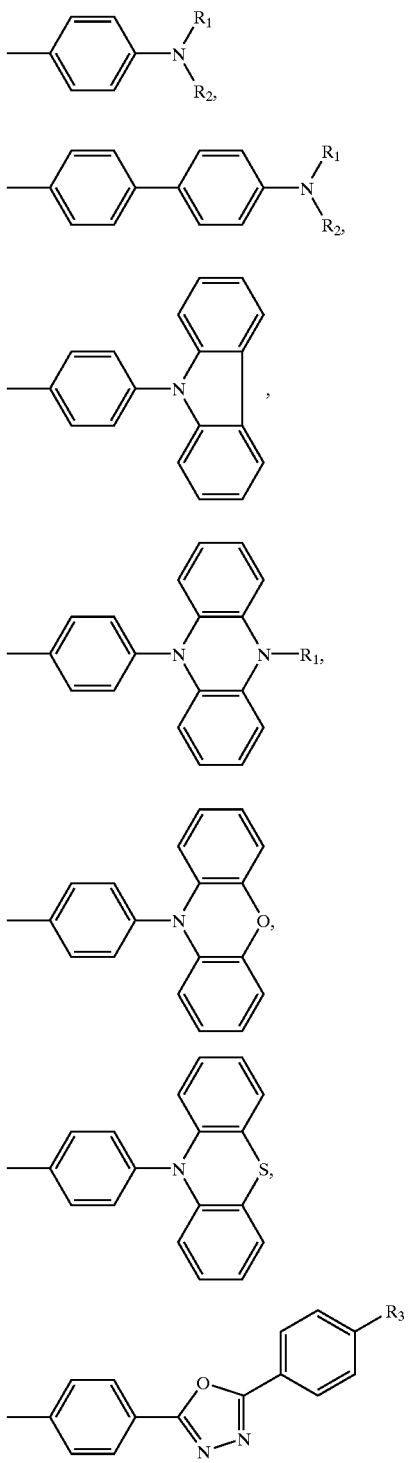

wherein $R_1$ and $R_2$ are independently at each occurrence selected from the group comprising straight chain $C_{1-20}$ alkyl, branched $C_{1-20}$ alkyl, aryl, substituted aryl, alkylaryl, substituted alkylaryl, alkoxyaryl, substituted alkoxyaryl, aryloxyaryl, substituted aryloxyaryl, dialkylaminoaryl, substituted dialkylaminoaryl, diarylaminoaryl and substituted diarylaminoaryl, and wherein $R_3$ is independently at each occurrence selected from the group comprising straight chain $C_{1-20}$ alkyl, branched $C_{1-20}$ alkyl, aryl, substituted aryl, alkylaryl and substituted alkylaryl.

In one embodiment it is preferred that the polyfluorene comprises about 0.5–9 percent by weight of charge-transporting moieties.

It is also preferred that the polyfluorene comprises about 0.5–9 mole percent of charge-transporting moieties.

In a particularly preferred embodiment $R_1$ and $R_2$ are independently at each occurrence selected from the group comprising 4-methylphenyl, 2-methylphenyl, phenyl, 1-naphthyl, 2-naphthyl, 4-methoxyphenyl, 2-methoxyphenyl, 4-dimethylaminophenyl, 2-dimethylaminophenyl, 4-diphenylaminophenyl and 4-phenoxyphenyl.

Preferred combinations are:
a) $R_1$=phenyl, $R_2$=4-methylphenyl;
b) $R_1$=phenyl, $R_2$=1-naphthyl;
c) $R_1$=phenyl, $R_2$=2-naphthyl;
d) $R_1$=$R_2$=4-methylphenyl;
e) $R_1$=$R_2$=phenyl;
f) $R_1$=$R_2$=4-dimethylaminophenyl;
g) $R_1$=$R_2$=4-diphenylaminophenyl.

The objects of the invention are also solved by a polyfluorene end-capped with at least one moiety selected from the group comprising

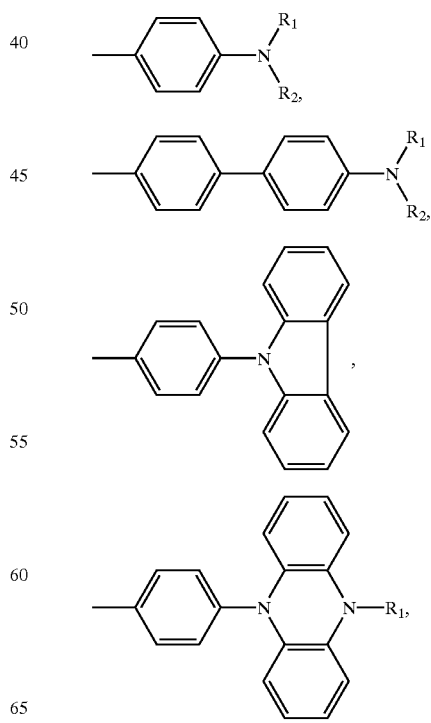

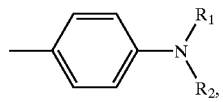

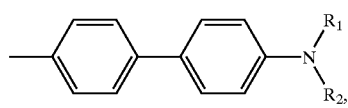

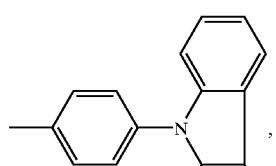

wherein $R_1$ and $R_1$ are independently at each occurrence selected from the group comprising straight chain $C_{1-20}$ alkyl, branched $C_{1-20}$ alkyl, aryl, substituted aryl, alkylaryl, substituted alkylaryl, alkoxyaryl, substituted alkoxyaryl, aryloxyaryl, substituted aryloxyaryl, dialkylaminoaryl, substituted dialkylaminoaryl, diarylaminoaryl and substituted diarylaminoaryl, and wherein $R_3$ is independently at each occurrence selected from the group comprising straight chain $C_{1-20}$ alkyl, branched $C_{1-20}$ alkyl, aryl, substituted aryl, alkylaryl and substituted alkylaryl.

In one embodiment it is preferred that the polyfluorene comprises about 0.5–9 percent by weight of charge-transporting moieties.

It is also preferred that the polyfluorene comprises about 0.5–9 mole percent of charge-transporting moieties.

In a preferred embodiment $R_1$ and $R_2$ are independently at each occurrence selected from the group comprising 4-methylphenyl, 2-methylphenyl, phenyl, 1-naphthyl, 2-naphthyl, 4-methoxyphenyl, 2-methoxyphenyl, 4-dimethylaminophenyl, 2-dimethylaminophenyl, 4-diphenylaminophenyl and 4-phenoxyphenyl.

Preferred combinations are:
a) $R_1$=phenyl, $R_2$=4-methylphenyl;
b) $R_1$=phenyl, $R_2$=1-naphthyl;
c) $R_1$=phenyl, $R_2$=2-naphthyl;
d) $R_1$=$R_2$=4-methylphenyl;
e) $R_1$=$R_2$=phenyl;
f) $R_1$=$R_2$=4-dimethylaminophenyl;
g) $R_1$=$R_2$=4-diphenylaminophenyl.

The objects of the present invention are further solved by a polyfluorene having the formula wherein $R_4$ and $R_5$ are independently at each occurrence selected from the group comprising:

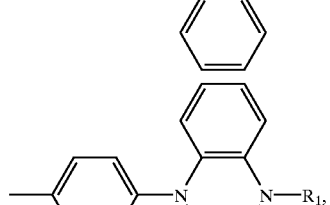

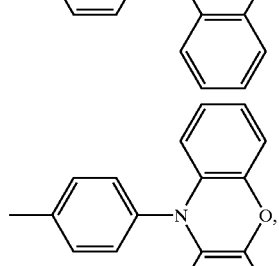

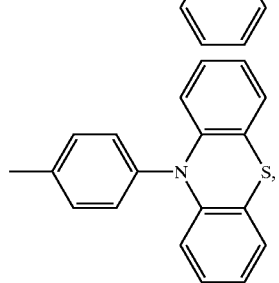

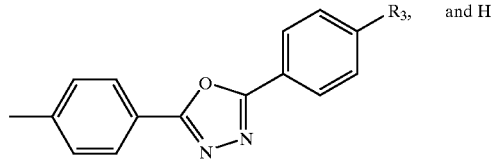

and H

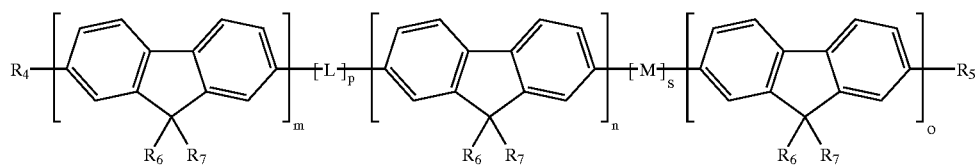

$R_1$ and $R_2$ being independently selected from the group comprising straight chain $C_{1-20}$ alkyl, branched $C_{1-20}$ alkyl, aryl, substituted aryl, alkylaryl, substituted alkylaryl, alkoxyaryl, substituted alkoxyaryl, aryloxyaryl, substituted aryloxyaryl, dialkylaminoaryl, substituted dialkylaminoaryl, diarylaminoaryl and substituted diarylaminoaryl, $R_3$ being selected from the group comprising straight chain $C_{1-20}$ alkyl, branched $C_{1-20}$ alkyl, aryl, substituted aryl, alkylaryl and substituted alkylaryl, and wherein $R_6$ and $R_7$ are independently at each occurrence selected from the group comprising straight chain $C_{1-20}$ alkyl, branched chain $C_{1-20}$ alkyl, aryl, substituted aryl, alkylaryl, substituted alkylaryl, —$(CH_2)_q$—$(O$—$CH_2$—$CH_2)_r$—$O$—$CH_3$, q being selected from the range $1 \leq q \leq 10$, r being selected from the range $0 \leq r \leq 20$, and wherein L and M are independently at each occurrence selected from the group comprising thiophene, substituted thiophene, phenyl, substituted phenyl, phenanthrene, substituted phenanthrene, anthracene, substituted anthracene, any aromatic monomer that can be synthesized as a dibromo-substituted monomer, benzothiadiazole, substituted benzothiadiazole, perylene and substituted perylene, and wherein $m+n+o \geq 10$, each of m, n, o being independently selected from the range 1–1,000, and wherein p is selected from the range 0–15, and wherein s is selected from the range 0–15, with the proviso that, if $R_4$ is H, $R_5$ is not H, and if $R_5$ is H, $R_4$ is not H.

In one embodiment a polyfluorene is preferred, wherein m, p, s, o are 0, and wherein $R_4$–$R_7$ and $R_1$–$R_3$ are as previously defined.

In one embodiment a polyfluorene is preferred which comprises about 0.5–9 percent by weight of $R_4$- and $R_5$-groups.

In one embodiment a polyfluorene is preferred which comprises about 0.5–9 mole percent of $R_4$- and $R_5$-groups.

It is preferred that a polyfluorene according to the present invention be cross-linked to a polyfluorene according to the present invention via at least one linkage selected from the group comprising a 9,9-spirobifluorene-linkage, a bifluorenyl-linkage, a bifluorenylidene-linkage and an $\alpha,\omega$-difluorenylalkane-linkage with a length of the alkane spacer in the range from 1–20 C-atoms.

It is also preferred that a polyfluorene according to the present invention has at least one color-tuning moiety incorporated into the main chain, wherein, more preferred, the color-tuning moiety is selected from the group comprising thiophene, substituted thiophene, phenyl, substituted phenyl, phenanthrene, substituted phenanthrene, anthracene, substituted anthracene, any aromatic monomer that can be synthesized as a dibromo-substituted monomer, benzothiadiazole, substituted benzothiodiazole, perylene and substituted perylene.

In one embodiment a polyfluorene is preferred which is liquid-crystalline, wherein, more preferred, it is liquid-crystalline at or above 70° C.

In another embodiment a polyfluorene is preferred, which is amorphous.

The objects of the present invention are furthermore solved by a polyfluorene selected from the group comprising

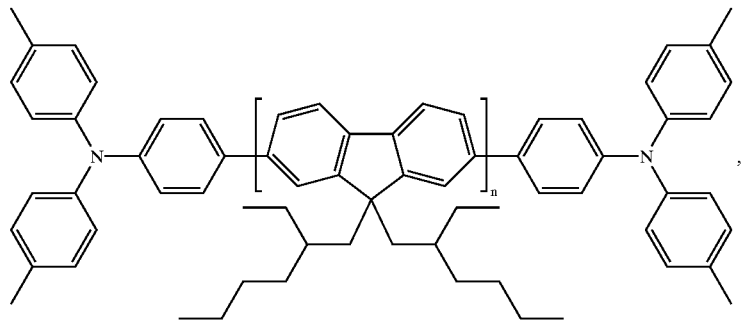

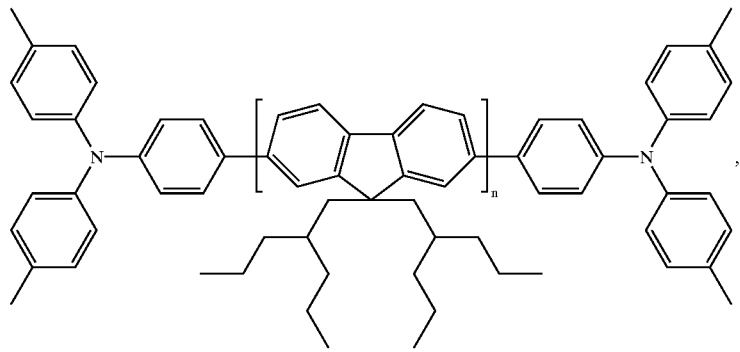

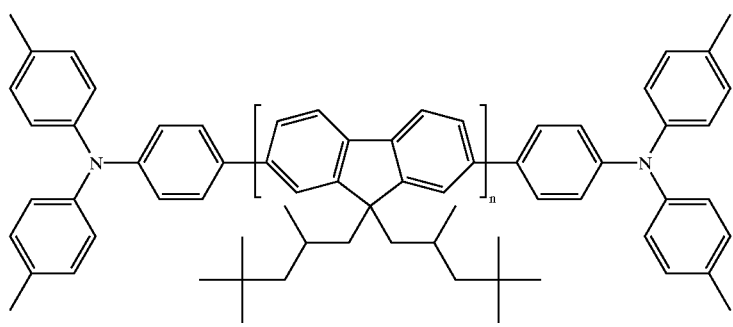
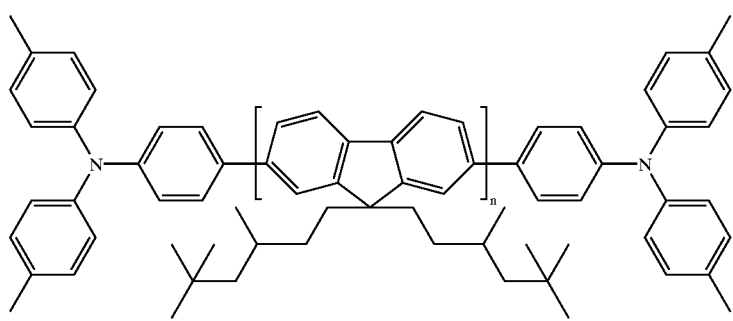
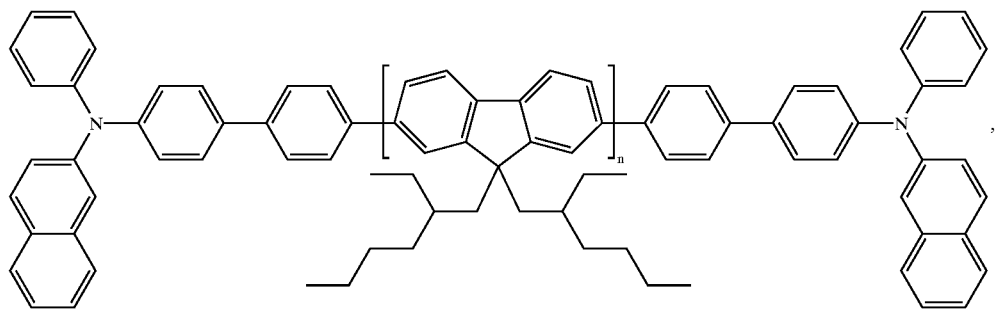
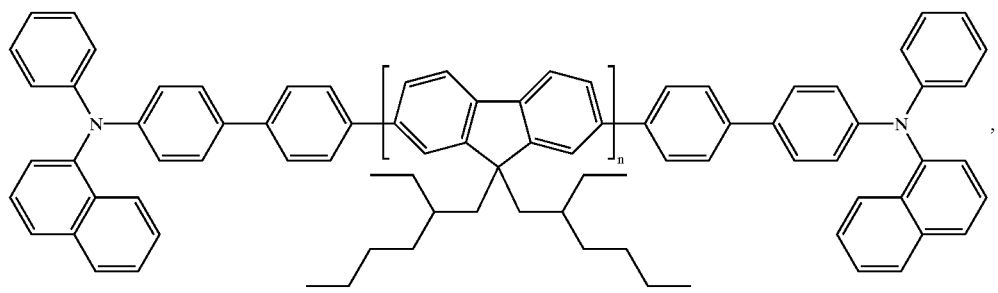
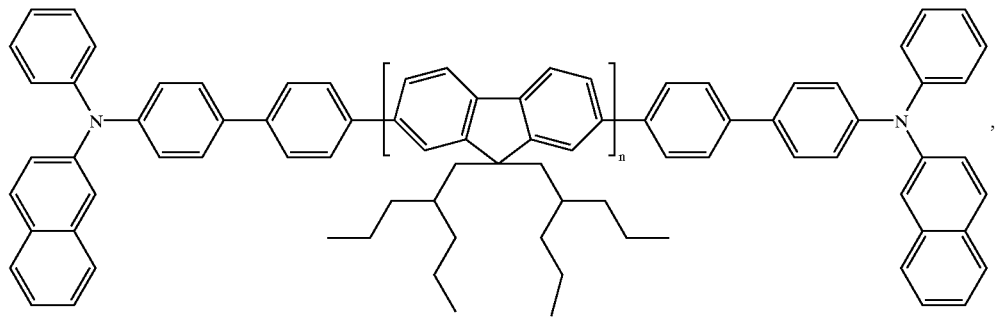

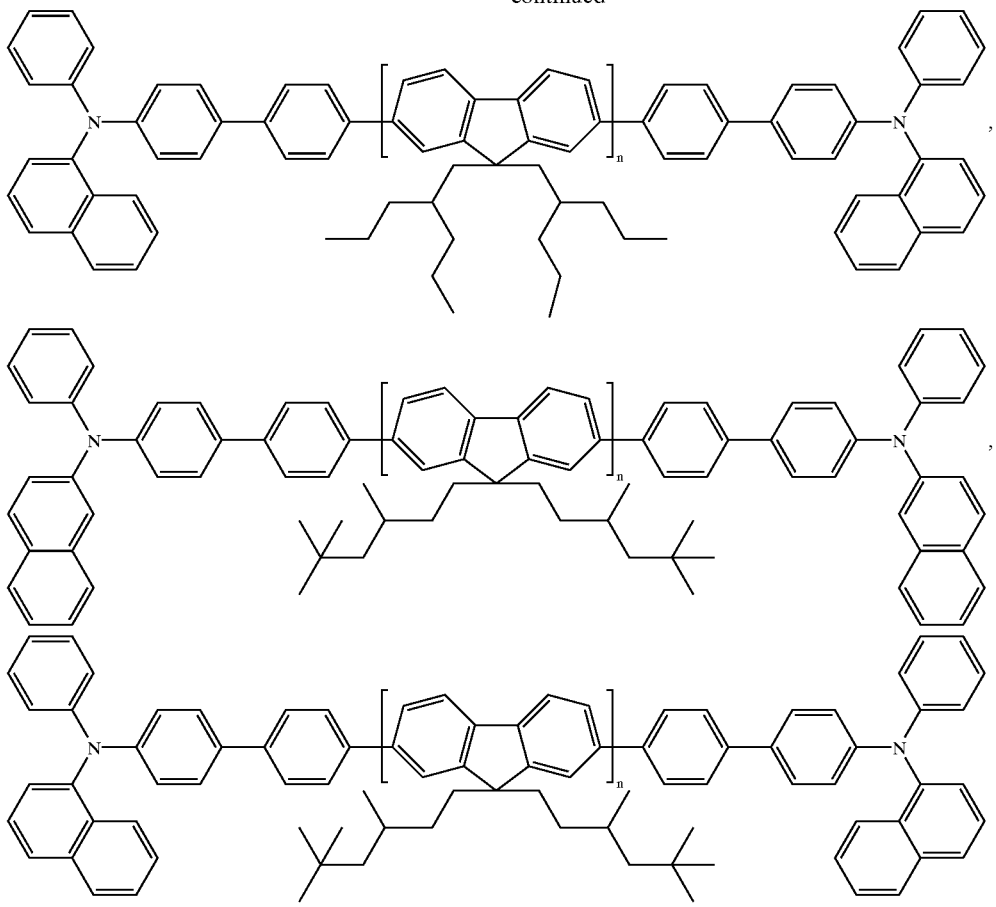

wherein n is as previously defined.

The objects of the present invention are also solved by a film incorporating a polyfluorene according to the present invention.

It is preferred that the film be aligned.

It is preferred that the film incorporates at least one other substance, wherein said other substance is selected from the group comprising fluorescent dyes, hole-transporting moieties, electron-transporting moieties, ion-transporting moieties, phosphorescent dyes, nanoparticles, low molecular weight liquid-crystalline moieties, other liquid-crystalline and/or fluorescent and/or phosphorescent and/or charge-transporting polymers.

In one embodiment it is preferred that the film be deposited on an alignment layer.

In one embodiment the film has a thickness ranging from 10 nm to 2 μm. In one embodiment it is preferred that the film has a thickness ranging from 50–300 nm.

The objects of the present invention are also solved by a device selected from the group comprising FETs, photovoltaic elements, LEDs and sensors, incorporating a polyfluorene according to the present invention.

It is preferred that the device has another polymer incorporated, wherein, more preferred, said polymer is a luminescent polymer.

The objects of the present invention are also solved by a device selected from the group comprising FETs, photovoltaic elements, LEDs and sensors, incorporating a film according to the present invention.

The objects of the present invention are also solved by the use of a polyfluorene according to the present invention in a film, wherein, more preferred, the film is an emission layer.

The objects of the present invention are also solved by the use of a polyfluorene according to the present invention in a device selected from the group comprising FETs, photovoltaic elements, LEDs and sensors.

The objects of the present invention are also solved by the use of a film according to the present invention in a device selected from the group comprising FETs, photovoltaic elements, LEDs, and sensors.

The objects of the present invention are also solved by the use of a device according to the present invention in combination with a liquid-crystal display (LCD).

It has surprisingly been found that end-capping a polyfluorene polymer main chain with charge-transporting moiety yields LEDs with a higher efficiency and a better colour stability, yet without altering the electronic properties of the polyfluorene polymer main chain. Furthermore, surprisingly, end-capping with appropriate charge-transporting groups does not disturb the phase property of the polyfluorene polymer and does not influence their orientational capabilities. A further advantage in connection with the present invention is the fact that end-capping the polyfluorene molecule with a charge-transporting moiety in the indicated weight-percent range or mole-percent range enables a precise control of the molecular weight of the polyfluorene.

The terms as used herein are defined as follows:

A molecule is "end-capped with" a group if the group is attached, preferably, covalently attached, to said molecule. The site of attachment can be any site in the molecule that renders the attached group a terminal group; in the case of a linear polymer the preferred site of end-capping are the two termini. Attachment-sites, however, other than the terminal sites are envisaged, too, such as attachment-sites for side chains. In a branched polymer the preferred sites for end-capping are the terminal sites of each branch of the polymer.

The term "charge-transporting moiety" is meant to designate any chemical moiety capable of facilitating the transport of electrons, holes (e. g. charge-deficiencies, particularly electron-deficiencies) and ions. The term furthermore comprises also those groups, that can be transformed into electron-transporting moieties, hole-transporting moieties or ion-transporting moieties, e. g. by protonation, cleavage, proteolysis, photolysis etc.

A "colour-tuning moiety" is any moietiy capable of modifying the spectral properties of a molecule to which such moiety is attached and/or into which such moiety is incorporated.

A "film" is any layer having a thickness selected from the range 10 nm–2 μm, preferably selected from 50–300 nm. Such a film can, e. g., be an emission layer of an optoelectronic device, e. g. an LED. The film can be aligned or non-aligned and prepared by, for example, casting from solution, spin casting, doctor-blading, offset printing, inkjet printing etc. The alignment is preferably achieved by annealing through heating above or close to the transition temperature to the liquid-crystalline phase, but other methods and ways of annealing and aligning are possible, for example by exposition to solvent vapor. The film can be deposited on a specific alignment layer for the purpose of alignment of the molecules in the film, or it can be aligned directly by techniques such as stretching, rubbing etc. Preferable materials for an alignment layer are selected from the group comprising polyimide, nylon, PVA, poly(p-phenylene vinylene), polyamide, teflon (hot rubbed) and glass, but are not restricted thereto. The alignment layer can have its properties induced by rubbing, illumination with polarized light, ion-bombardment, surface-structure induction by grating etc. In a device according to the present invention a film according to the present invention can be used in conjunction with at least one other layer, e. g. another emission layer or several other emission layers, depending on the requirements of the application (in addition to the other layers whose presence is inherently essential for the proper functioning of the device).

The term "in combination with a liquid-crystal display" is meant to designate any arrangement in which a film and/or a device according to the present invention is in physical proximity to a liquid-crystal display (LCD) and/or functionally coupled thereto, e. g. the use of an LED, preferably an LED emitting polarized light, as a backlight for a liquid-crystal display.

The invention is now being described more fully in the following specific description and the following figures, wherein FIG. 1 shows a general synthetic route to poly(9,9-dialkylfluorene-2,7-diyl)s;

FIG. 2 shows luminance-voltage curves for LEDs with emission layers of pure poly(2,7-(9,9-bis(2-ethylhexyl)) fluorene (PF2/6_1) and poly(2,7-(9,9-bis(2-ethylhexyl)) fluorene)-2,7-bis(4-methylphenyl)phenylamine end-capped with different concentrations (2, 4, 9 mol %) of the hole-transporting end-capper (PF2/6am2, PF2/6am4; PF2/6am9); the inset of FIG. 2 shows luminescence-current density curves for the same devices;

FIG. 3 shows normalized electroluminescence spectra of the devices with active layers of pure poly(2,7-(9,9-bis(2-ethylhexyl))fluorene (PF2/6_1 & PF 2/6_2) with different molecular weights and poly(2,7-(9,9-bis(2-ethylhexyl)) fluorene)-2,7-bis(4-methylphenyl)phenylamine (PF2/6am2; PF2/6am4; PF2/6am9) with different concentrations of the hole-transporting end-capper;

Figure 1:
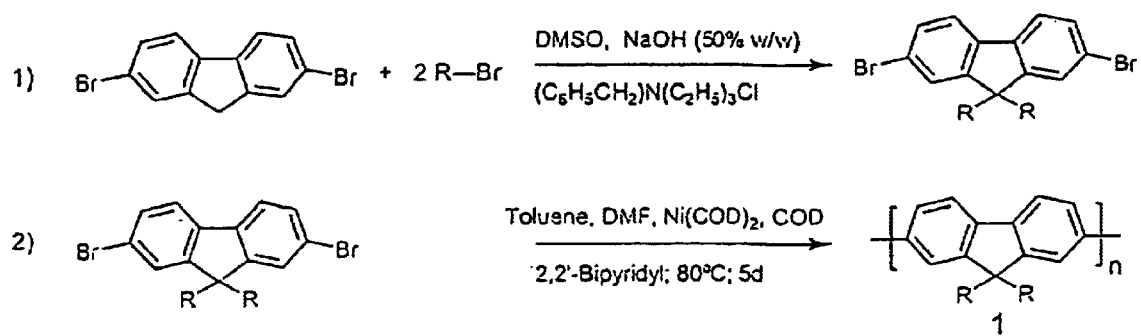

The following non-limiting examples describe the present invention more fully and in a more detailed manner without being intended to limit the present invention.

EXAMPLES

Example 1

Synthesis of Monomers

The synthesis of high molecular weight, soluble polyfluorenes by transition metal catalyzed aryl-aryl coupling was firstly described by Pei and Yang from UNIAX Corp. (Y. Yang, Q. Pei; *J. Am. Chem. Soc.*, 118, 7416 (1996)). The materials used for device fabrication were synthesized according to general procedures for Yamamoto-type reductive polycondensations of dihaloaromatic compounds with Ni(COD)$_2$ as an effective aryl-aryl coupling agent (T. Yamamoto; *Progr. Polym. Sci.*, 17, 1153 (1992)). The 9,9-dialkyl-substituted monomers were prepared in close analogy to literatures methods ((a) E. P. Woo, M. Inbasekaran, W. Shiang, G. R. Roof; *Int. Pat. Appl.* WO97/05184 (1997); (b) M. Inbasekaran, W. Wu, E. P. Woo; U.S. Pat. No. 5,777,070 (1998)). Where required, a primary alcohol was converted into the corresponding alkylbromide prior to the alkylation of 2,7-dibromofluorene.

Example 2

Synthesis of End-capped Polymers

At the beginning bis(4-methylphenyl)(4-bromophenyl) amine was added to the reaction mixture at a concentration of 2–9 mol/l as a suitable monofunctional end capping reagent to the reaction mixture. The resulting polymers were precipitated in a mixture of methanol/acetone/conc. hydrochloric acid and extracted with ethylacetate for 5 days. Finally the polymers were redissolved in toluene, the solvent partially evaporated, the polymers reprecipitated and dried in vacuum at 80° C. Yields are between 50%–80%.

The monofunctionality of the end-capping reagent ensured that the polymer was terminated upon reaction with such reagent. According to this synthetic procedure none of the end-capping moieties will therefore be incorporated into the bulk of the main chain. Instead the end-capping moiety will come to lie exclusively at the termini of the polymer.

The following polymers were prepared according to this procedure:

Poly(2,7-(9,9-bis(2-ethylhexyl))fluorene)-2,7-bis(4-methylphenyl)phenylamine [PF2/6am]:

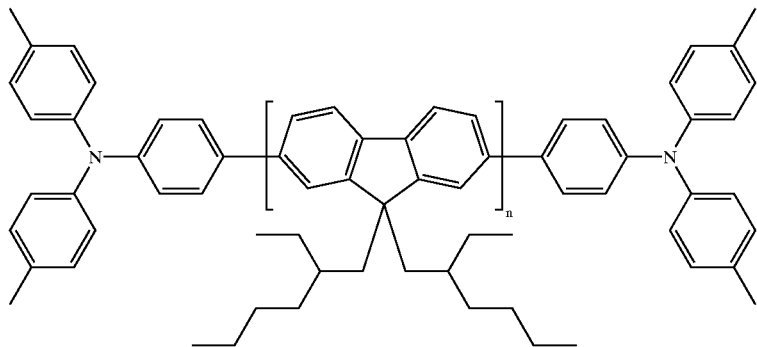

Poly(2,7-(9,9-bis(2-propylpentyl))fluorene)-2,7-bis(4-methylphenyl)phenylamine) [PF3/5am]:

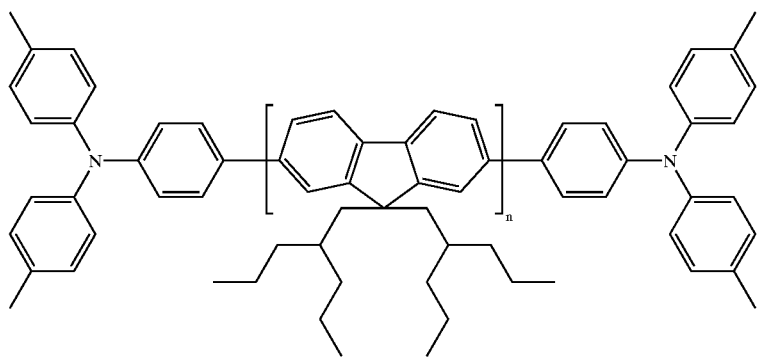

Poly(9,9-bis(2,4,4-trimethylpentyl)fluorene)-2,7-bis(4-methylphenyl)phenylamine [PF3/1/5am]:

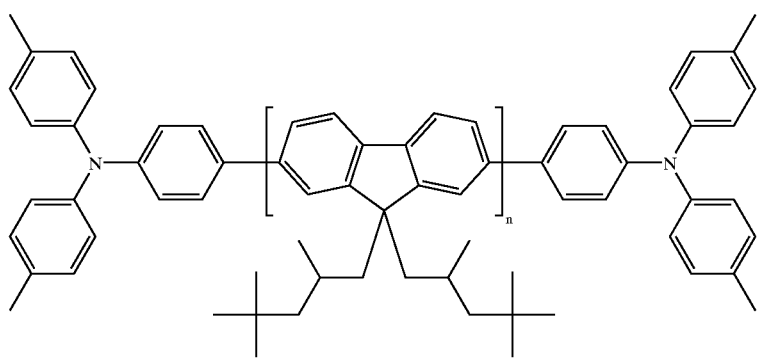

Poly(9,9-bis(3,5,5-trimethylhexyl)fluorene)-2,7-bis(4-methylphenyl)phenylamine [PF3/1/6am]:

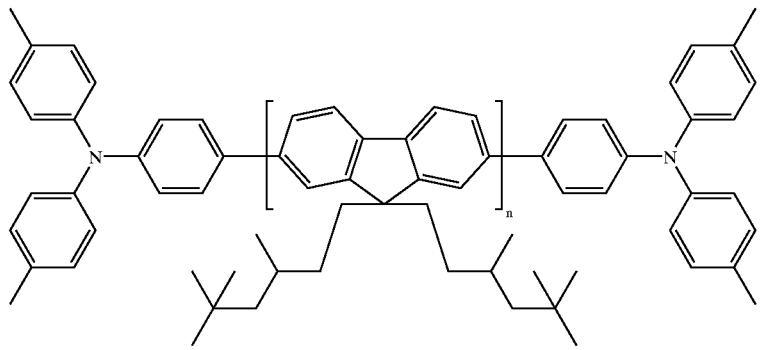

Summary of investigated end capped polyfluorenes. Gel-permeation chromatography (GPC) was carried out in THF with polystyrene standard:

| | Ratio Monomer: End Capper (in the beginning of polymerization reaction) | $M_n$ (g/mol) | $M_w$ (g/mol) | D |
|---|---|---|---|---|
| PF2/6am2 | 98:2 | 102000 | 145000 | 1.42 |
| PF2/6am4 | 96:4 | 48400 | 75100 | 1.55 |
| PF2/6am9* | 91:9 | 12000 | 30800 | 2.57 |
| PF3/5am6 | 94:6 | 29500 | 54300 | 1.84 |
| PF3/1/5am4 | 96:4 | 32000 | 61500 | 1.92 |
| PF3/1/6am2 | 98:2 | 70800 | 137300 | 1.94 |

*The polymer was extracted with acetone instead of ethylacetate.

Example 3

Fabrication of LED Devices

Single layer LEDs were prepared from the pure PF2/6 and from PF2/6 end-capped with 2, 4 and 9 mol % triphenylamine-PF2/6am2, PF2/6am4 and PF2/6am9, respectively. Pure PF3/5 and end-capped PF3/5am, as well as pure PF3/1/5 and end-capped PF3/1/5am were also investigated. All devices were fabricated at ambient conditions by spin-casting the polymer solution in toluene onto glass substrates covered by patterned ITO electrodes and a 25 nm layer of the conducting polymer polyethylenedioxythiophene (PEDT). Samples were dried in vacuum at room temperature for 24 hours prior to evaporation of Ca/Al top electrodes. Typical emission layer thicknesses (as measured with a Tencor α-step profiler) were 90 nm. The overlap between the two electrodes resulted in device areas of 5 mm². The device characterization was carried out in an evacuated sample chamber.

Example 4

Device Characteristics of LEDs Based on PF2/6am

Figure 2:
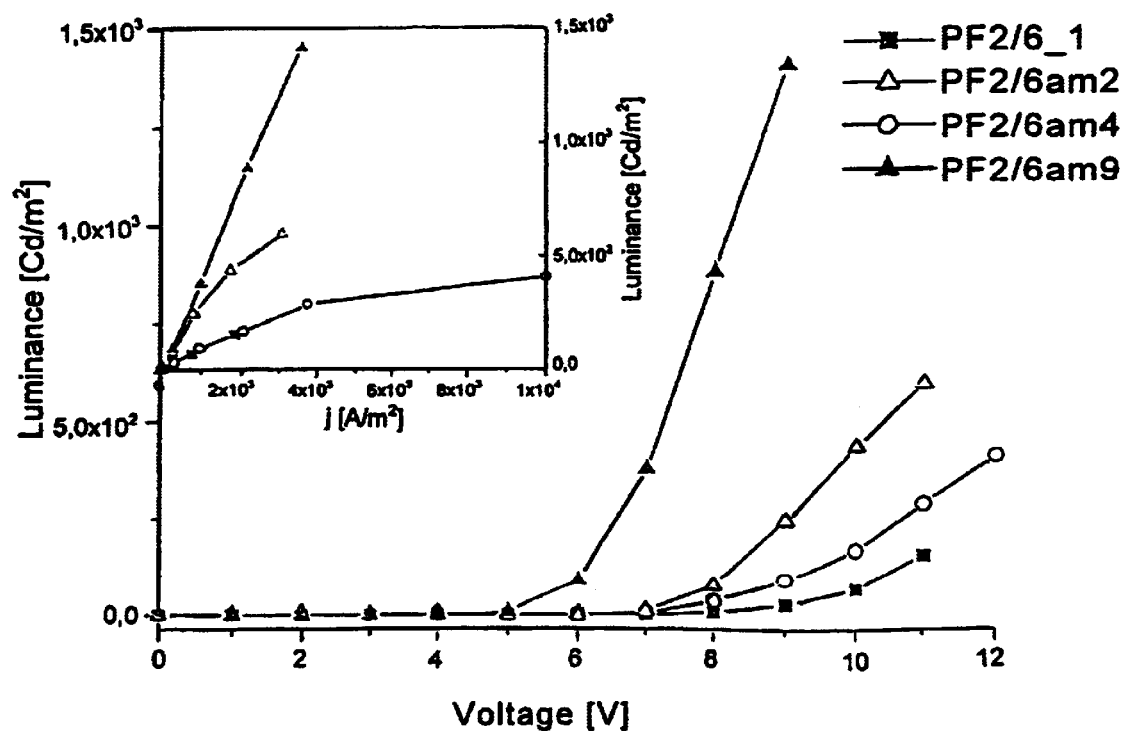

The luminance-voltage curves of the devices with active layers of PF2/6am2, PF2/6am4, and PF2/6am9 are shown in FIG. 2. Also displayed are the device characteristics of a device with the emission layer based on non end-capped polyfluorene (PF2/6_1, $M_n$=195 000). The brightness at 9 V increases from ca. 50 cd/m² for the non end-capped polymer up to 1500 cd/m² for the PF2/6 with 9 mol % end-capper. The insert plot shows the increase in efficiency with increasing end-capper concentration—up to ca. 0.4 Cd/A at 1500 cd/m² for the device with the highest end-capper content. The deviations for the sample with 4 mol % end-capper could be due to the higher degree of crystallinity of the emission layer formed by this polymer.

Example 5

Spectral Characteristics of LEDs Based on PF2/6am

Figure 3:
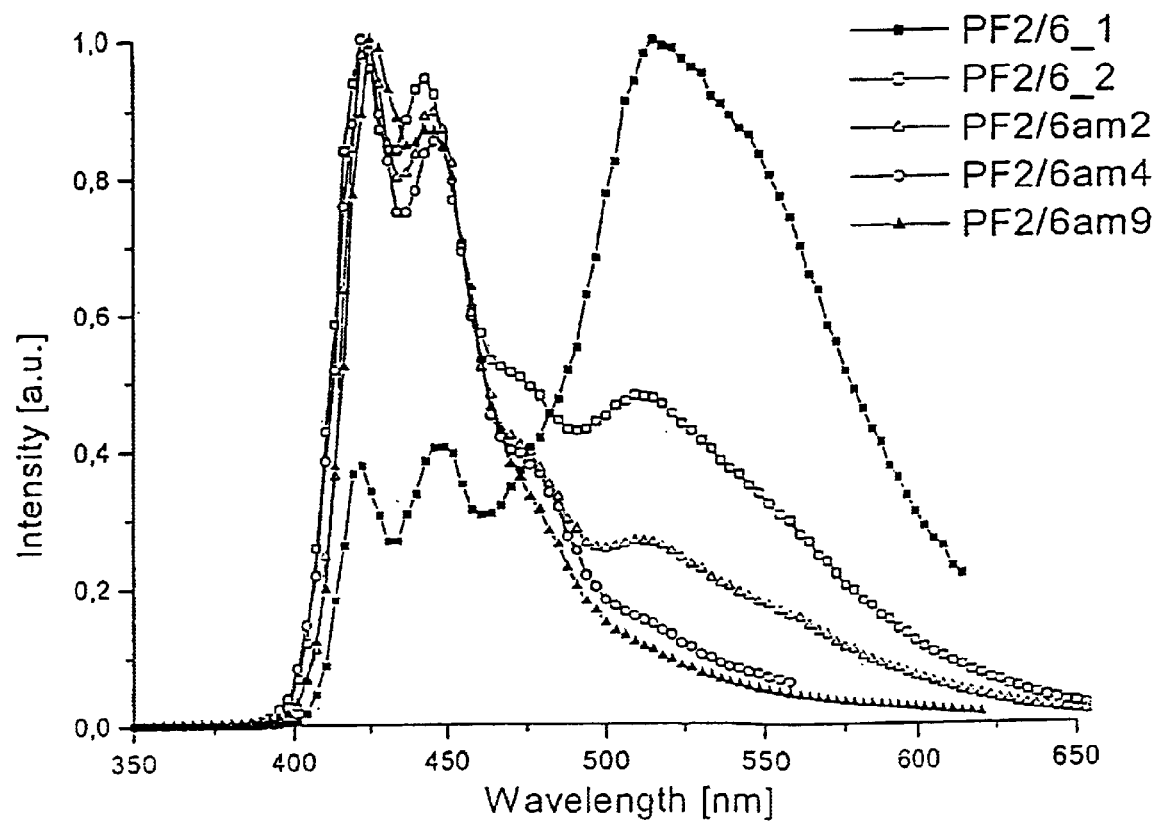

Emission spectra were recorded on a E686 Princeton Applied Research Model 1235 digital triple grating spectrograph for devices with emission layers based on PF2/6am2, PF2/6am4, PF2/6am9, PF2/6_1 and a homopolymer with a molecular weight $M_n$=100 000 (PF2/6_2). Three main peaks can be identified in the PF EL-spectrum shown in FIG. 3: exciton emission at ca. 422 nm and 448 nm (zero phonon line and its vibronic progression) and a broad band at ca. 517 nm. For the pure PF2/6 with a higher molecular weight (PF2/6_1) the EL spectrum is entirely governed by the red-shifted emission at ca. 520 nm, with significant variations from sample to sample. The hole-transporting end-capper (HTE) content significantly affects the EL spectra of PF2/6am as shown in FIG. 3. Upon increasing the end-capper concentration, the intensity of the vibronic progression becomes smaller and the red contribution at 517 nm is fully suppressed. It is to be noted that PF2/6am2 with 2 mol % hole-transporting end-capper has approx. the same $M_n$ as the non-end-capped PF2/6_2.

Example 6

Device Characteristics and Spectral Properties of LEDs Based on PF3/1/5am

Figure 4:
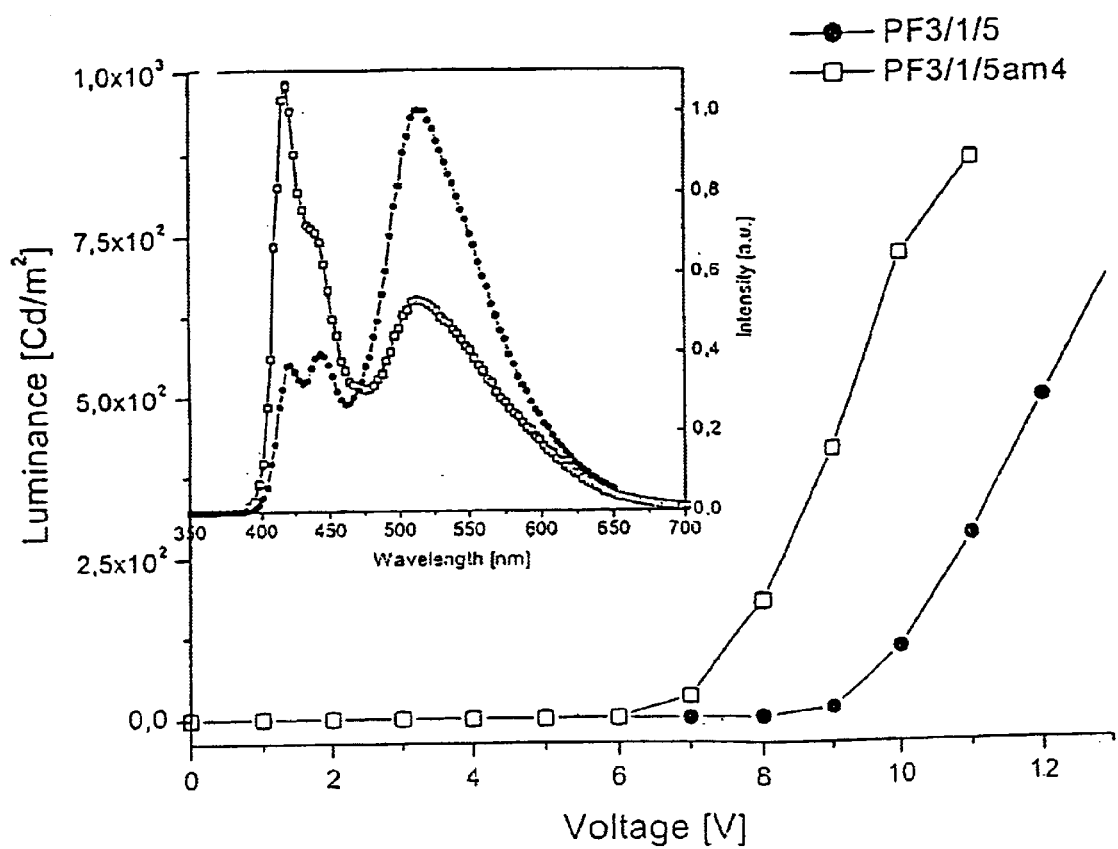
FIG. 4 shows luminance-voltage curves for LEDs with emission layers of pure poly(9,9-bis(2,4,4-trimethylpentyl) fluorene (PF3/1/5) and poly(9,9-bis(2,4,4-trimethylpentyl) fluorene-2,7-bis-(4-methylphenyl)phenylamine (PF3/1/5am4) end-capped with 4 mol % end-capper; the inset shows normalized electroluminescent spectra of the same devices.

Similar effects are observed for the polyfluorene with symmetrical but bulky side-chain pattern (PF3/1/5) as shown in FIG. 4. Upon end-capping with 4 mol % HTE, the onset voltage for electroluminescence becomes smaller and the device brightness increases. The blue excitonic emission band at 422 nm representing the inherent characteristics of polyfluorenes becomes more pronounced and the red contribution at ca. 517 nm is strongly suppressed. The $M_n$ of the non-end-capped PF3/1/5 was 80 000.

Example 7

Device Characteristics and Spectral Properties of LEDs Based on PF3/5am

The PF3/5 polymer has the highest tendency to crystallize because of its highly symmetric and less bulky side-chains.

Figure 5:
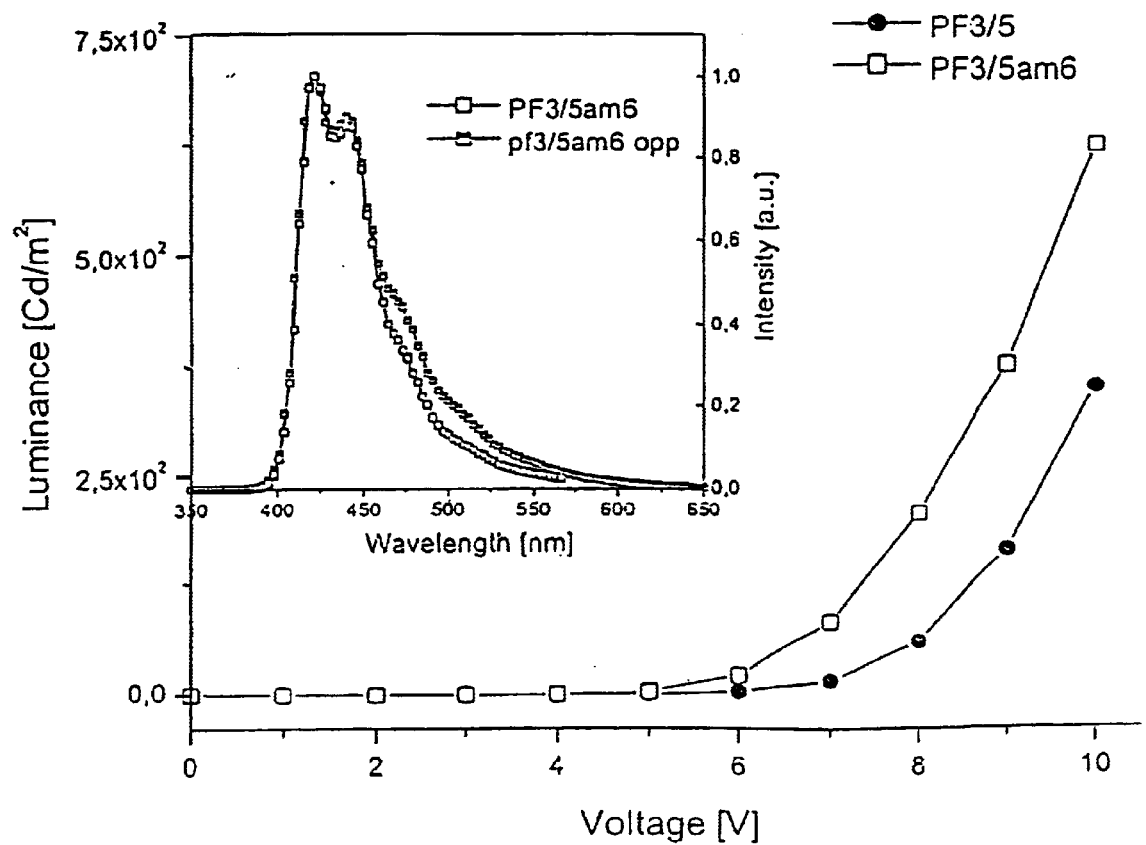
FIG. 5 shows luminance-voltage curves for LEDs with emissive layers of pure poly(2,7-(9,9-bis(2-propylpentyl)) fluorene (PF3/5) and poly(2,7-(9,9-bis(2-propylpentyl)) fluorene-2,7-bis(4-methylphenyl) phenylamine (PF3/5am6) end-capped with 6 mol % end-capper; the inset shows normalized electroluminescent spectra of the device with end-capped polymer fresh and after 15 minutes of operation.

The onset voltage for EL from devices with an PF3/5am6 emission layer is significantly lower compared to that of PF3/5 devices and the device brightness is higher as can be seen in FIG. 5. The EL spectrum of the non end-capped PF3/5 does not contain a red-shifted emission contribution but the colour stability is better for the end-capped PF3/5am6—there is practically no change in the device emission after more than 15 min operation (PF3/5am6=0 min; pf3/5am6 opp=15 min operation) as can be seen from the insert in FIG. 5.

In general, all of the devices comprising active layers of polyfluorenes end-capped with a charge-transporting moiety demonstrate stable colour characteristics.

Example 8

Alignment of PF2/6am

Figure 6:
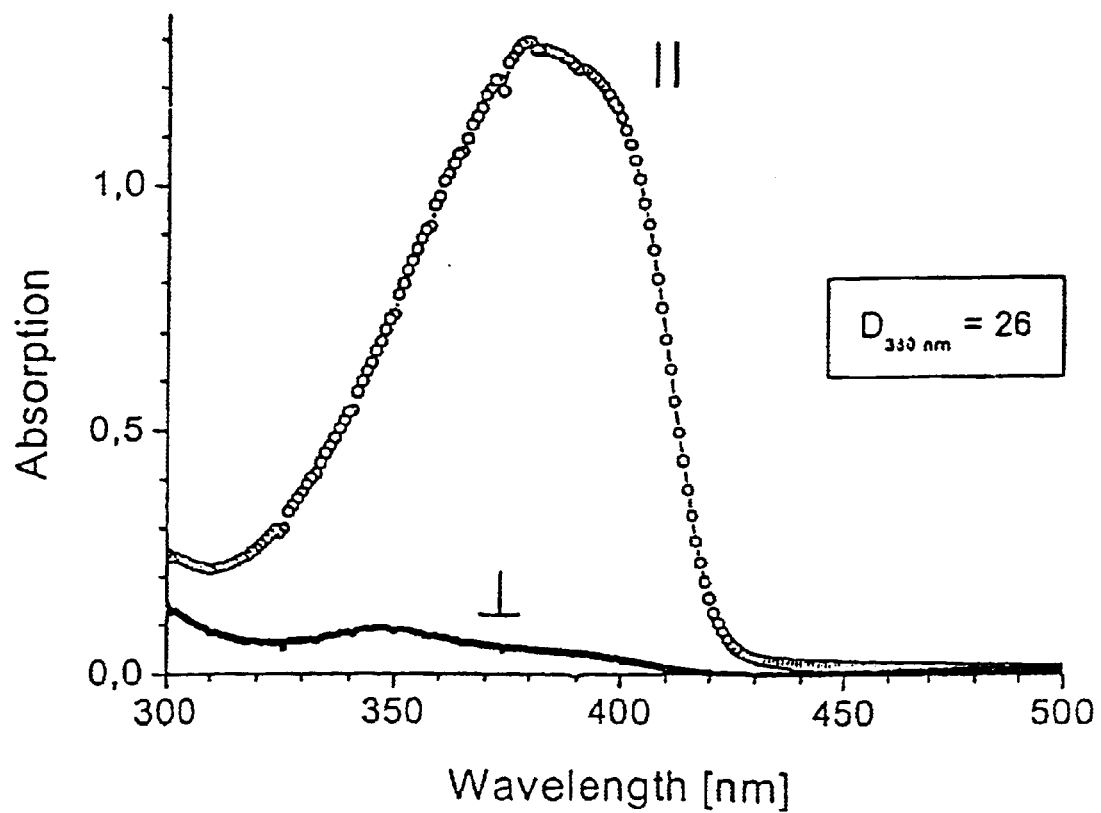
FIG. 6 shows the polarized absorption of a ca. 100 nm thick aligned layer of poly(2,7-(9,9-bis(2-ethylhexyl)) fluorene-2,7-bis(4-methylphenyl)phenylamine (PF2/6am4) with 4 mol % end-capper on rubbed polyimide annealed at 145° under Argon.

Polyimide (PI) alignment layers were prepared by spin casting of a PI precursor at a total solid content of 30 g/L in the Merck-ZLI 2650 kit solvent at 2000 rpm for 50 s. After 15 min. soft-baking at 80° C., the precursor was converted at 300° C. for 1 hr. under rotary pump vacuum. PI layers were rubbed unidirectionally using a rubbing machine from E.H.C. Co., Ltd., Japan. The rotating cylinder was covered with a rayon cloth and rotated at 1400 rpm. The samples were passed twice under the cylinder at a translating speed of 2.2 mm/s. The depth of impression of the rubbing cloth onto the substrate was approximately 0.8 mm. Films of PF2/6am were spun of 10 g/l toluene solution onto rubbed PI alignment layers. The final film thickness were 90 nm as measured with an Tencor α-step profiler. To induce monodomain alignment, films were annealed in an autoclave at a temperature of 145° C. for two hours in a 0.1 bar Ar-atmosphere and cooled to room temperature at a rate of 5 K/min. As can be seen in FIG. 6 a dichroic ratio of 26 at 380 nm was obtained.

Example 9

Preparation of LEDs with Aligned Emission Layer

Polyimide precursor modified for hole transport was spin cast on ITO patterned glass substrates. Conversion, rubbing, spin coating of PF2/6am, and annealing were done as described in example 8. Ca/Al top electrodes were thermally evaporated. The overlap between the two electrodes resulted in device areas of 5 mm². The device characterization was carried out in an evacuated sample chamber.

Example 10

Device Characteristics and Spectral Properties of Polarized LEDs

Figure 7:
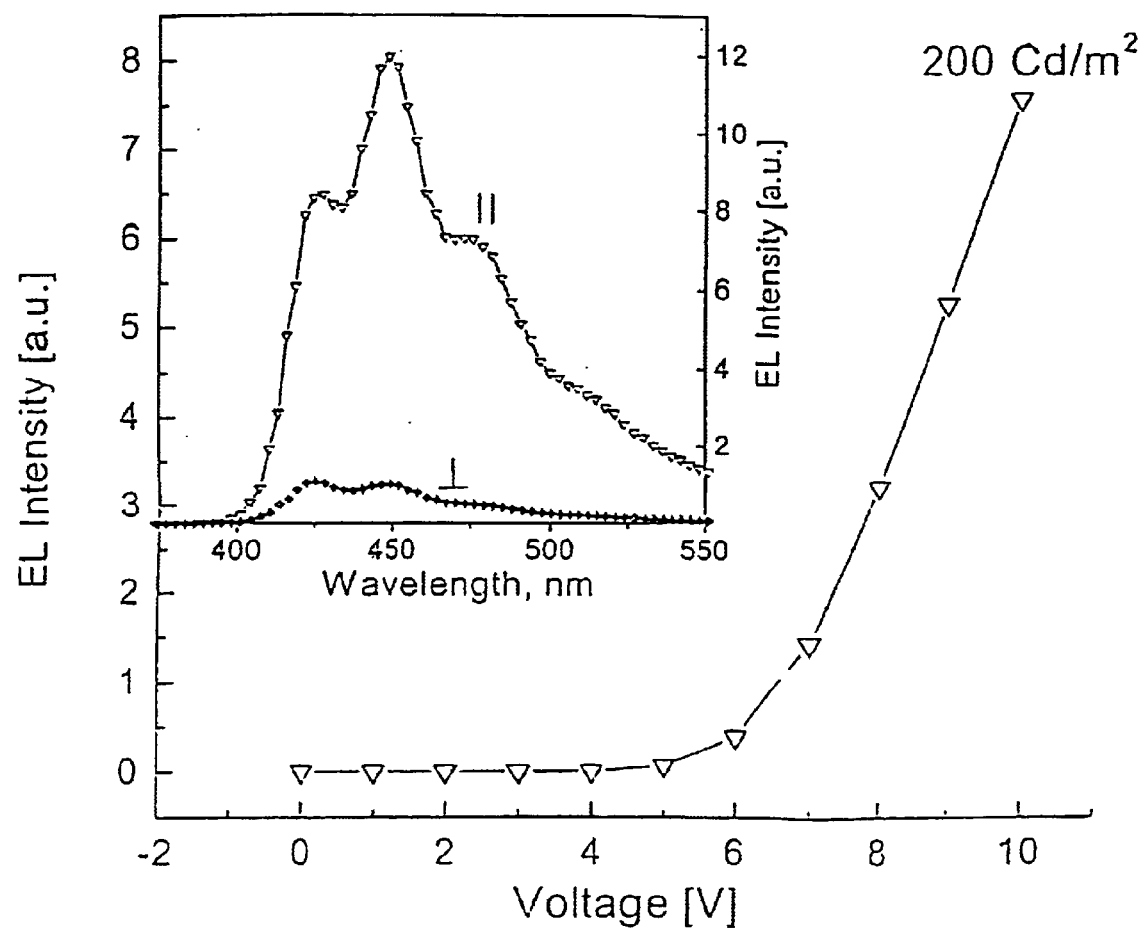
FIG. 7 shows an intensity-voltage curve for a polarized LED with an aligned poly(2,7-(9,9-bis(2-ethylhexyl)) fluorene-2,7-bis(4-methylphenyl)phenylamine (PF2/6am4), 4 mol % end-capper, emission layer; the inset shows emission spectra of the same device measured parallel and perpendicular to the rubbing direction of the hole-transporting layer.

The luminance-voltage curve of a typical polarized LED with an active layer of PF2/6am4 aligned on a hole transporting alignment layer is shown in FIG. 7. The device has an onset voltage for the polarized emission as low as 4.5 V, a brightness in excess of 200 Cd/m² at 10 V and a polarization ratio of the light emitted at 447 nm higher than 11 (see insert plot of FIG. 7).

The features disclosed in the foregoing description and the claims may, both separately and in any combination thereof be material for realising the invention in diverse forms thereof.

What is claimed is:

1. A polyfluorene end-capped with at least one charge-transporting moiety, wherein said charge transporting moiety is a chemical moiety adapted to facilitate the transport of electrons, holes or ions.

2. The polyfluorene according to claim 1, wherein the charge-transporting moiety is selected from the group consisting of electron-transporting moieties, hole-transporting moieties and ion-transporting moieties.

3. The polyfluorene according to claim 1, wherein the charge-transporting moiety is selected from the group consisting of:

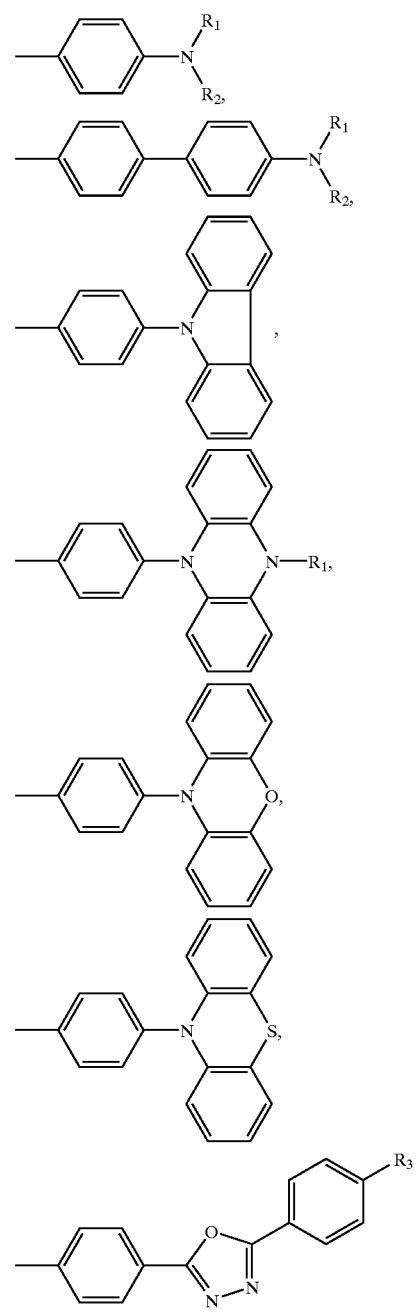

wherein $R_1$ and $R_2$ are independently at each occurrence selected from the group consisting of straight chain $C_{1-20}$ alkyl, branched $C_{1-20}$ alkyl, aryl, substituted aryl, alkylaryl, substituted alkylaryl, alkoxyaryl, substituted alkoxyaryl, aryloxyaryl, substituted aryloxyaryl, dialkylaminoaryl, substituted dialkylaminoaryl, diarylaminoaryl and substituted diarylaminoaryl, and wherein R₃ is independently at each occurrence selected from the group consisting of straight chain $C_{1-20}$ alkyl, branched $C_{1-20}$ alkyl, aryl, substituted aryl, alkylaryl and substituted alkylaryl.

4. The polyfluorene according to claim 3, wherein $R_1$ and $R_2$ are independently at each occurrence selected from the group consisting of 4-methylphenyl, 2-methylphenyl, phenyl, 1-naphthyl, 2-naphthyl, 4-methoxyphenyl, 2-methoxyphenyl, 4-dimethylaminophenyl, 2-dimethylaminophenyl, 4-diphenylaminophenyl and 4-phenoxyphenyl.

5. A polyfluorene end-capped with at least one moiety selected from the group consisting of:

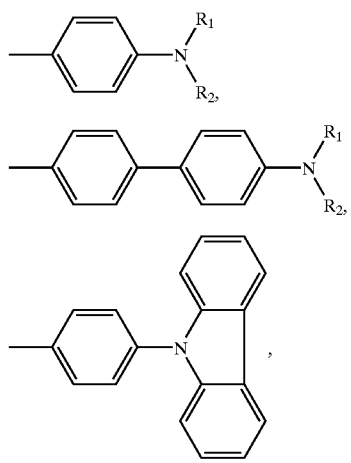

-continued

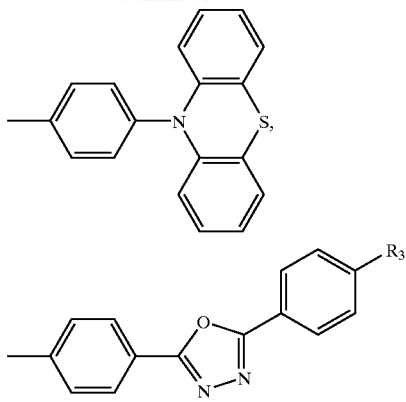

wherein $R_1$ and $R_2$ are independently at each occurrence selected from the group consisting of straight chain $C_{1-20}$ alkyl, branched $C_{1-20}$ alkyl, aryl, substituted aryl, alkylaryl, substituted alkylaryl, alkoxyaryl, substituted alkoxyaryl, aryloxyaryl, substituted aryloxyaryl, dialkylaminoaryl, substituted dialkylaminoaryl, diarylaminoaryl and substituted diarylaminoaryl, and wherein $R_3$ is independently at each occurrence selected from the group consisting of straight chain $C_{1-20}$ alkyl, branched $C_{1-20}$ alkyl, aryl, substituted aryl, alkylaryl and substituted alkylaryl.

6. The polyfluorene according to claim 5, wherein $R_1$ and $R_2$ are independently at each occurrence selected from the group consisting of 4-methylphenyl, 2-methylphenyl, phenyl, 1-naphthyl, 2-naphthyl, 4-methoxyphenyl, 2-methoxyphenyl, 4-dimethylaminophenyl, 2-dimethylaminophenyl, 4-diphenylaminophenyl and 4-phenoxyphenyl.

7. A polyfluorene having the formula

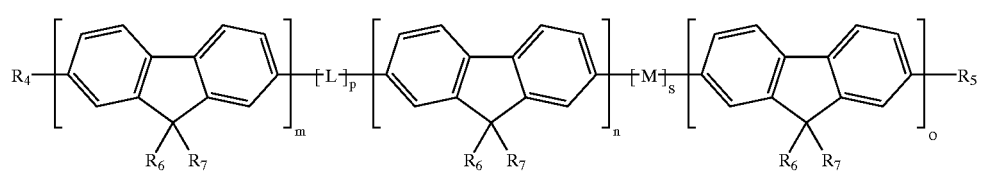

wherein $R_4$ and $R_5$ are independently at each occurrence selected from the group consisting of:

-continued

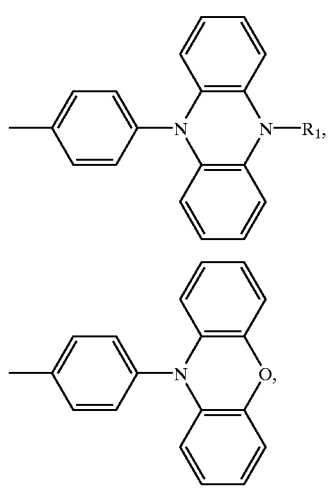

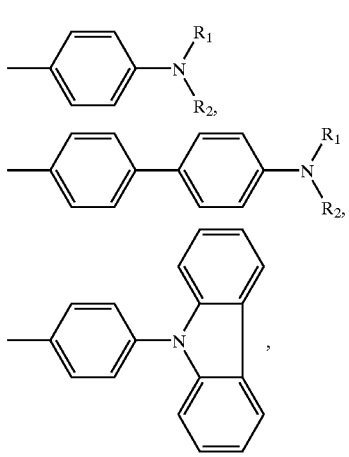

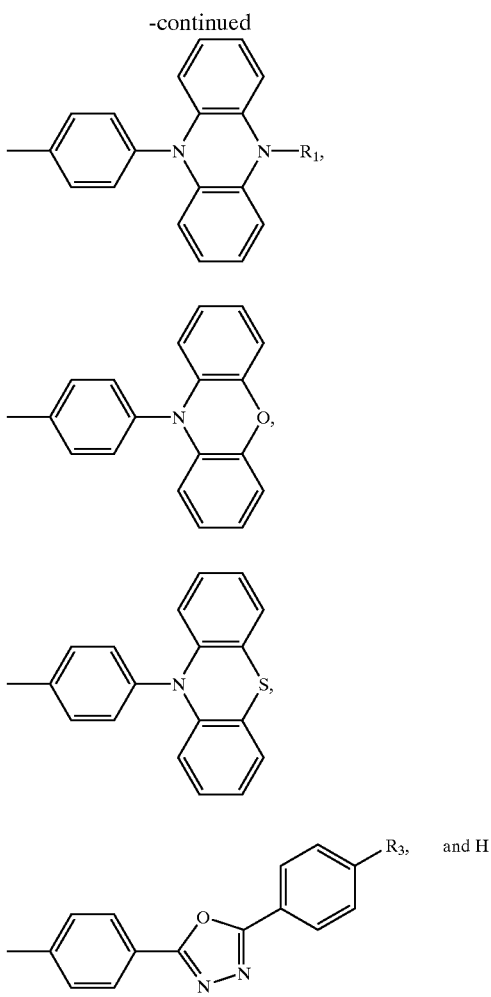

$R_1$ and $R_2$ being independently selected from the group consisting of straight chain $C_{1-20}$ alkyl, branched $C_{1-20}$ alkyl, aryl, substituted aryl, alkylaryl, substituted alkylaryl, alkoxyaryl, substituted alkoxyaryl, aryloxyaryl, substituted aryloxyaryl, dialkylaminoaryl, substituted dialkylaminoaryl, diarylaminoaryl and substituted diarylaminoaryl, $R_3$ being selected from the group consisting of straight chain $C_{1-20}$ alkyl, branched $C_{1-20}$ alkyl, aryl, substituted aryl, alkylaryl and substituted alkylaryl, and wherein $R_6$ and $R_7$ are independently at each occurrence selected from the group consisting of straight chain $C_{1-20}$ alkyl, branched chain $C_{1-20}$ alkyl, aryl, substituted aryl, alkylaryl, substituted alkylaryl, —$(CH_2)_q$—$(O—CH_2—CH_2)_r$—$O—CH_3$, q being selected from the range 1–10, r being selected from the range 0–20, and wherein L and M are independently at each occurrence selected from the group consisting of thiophene, substituted thiophene, phenyl, substituted phenyl, phenanthrene, substituted phenanthrene, anthracene, substituted anthracene, any aromatic monomer that can be synthesized as a dibromo-substituted monomer, benzothiadiazole, substituted benzothiadiazole, perylene and substituted perylene, and wherein m+n+o 10, each of m, n, o being independently selected from the range 1–1,000, and wherein p is selected from the range 0–15, and wherein s is selected from the range 0–15, with the proviso that, if $R_4$ is H, $R_5$ is not H, and if $R_5$ is H, $R_4$ is not H.

8. A polyfluorene according to claim 7,
wherein m, p, s, o are 0, and
wherein $R_4$–$R_7$ and $R_1$–$R_3$ are as previously defined.

9. The polyfluorene according to claim 7 cross-linked to a polyfluorene according to claim 7 via at least one linkage selected from the group consisting of a 9,9-spirobifluorene-linkage, a bifluorenylidene-linkage, a bifluorenylidene-linkage and an α,ω-difluorenylalkane-linkage with a length of the alkane spacer in the range from 1–20 C-atoms.

10. The polyfluorene according to claim 7 which has at least one color-tuning moiety.

11. The polyfluorene according to claim 10, wherein the color-tuning moiety is selected from the group consisting of thiophene, substituted thiophene, phenyl, substituted phenyl, phenanthrene, substituted phenanthrene, anthracene, substituted anthracene, any aromatic monomer that can be synthesized as a dibromo-substituted monomer, benzothiadiazole, substituted benzothiodiazole, perylene and substituted perylene.

12. The polyfluorene according to claim 7, wherein the polyfluorene is liquid-crystalline.

13. The polyfluorene according to claim 12, wherein the polyfluorene is liquid-crystalline at or above 70° C.

14. The polyfluorene according to claim 7, wherein the polyfluorene is amorphous.

15. The polyfluorene selected from the group consisting of:

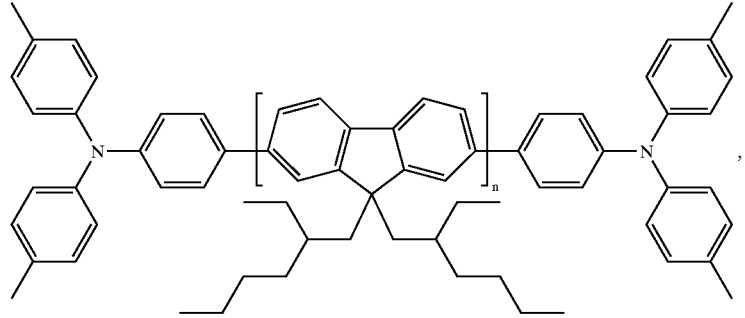

-continued
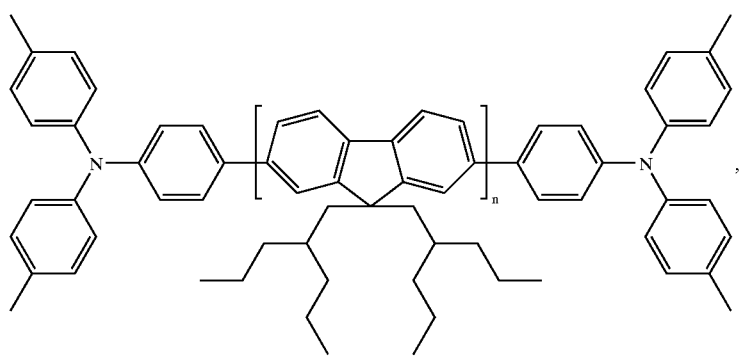,
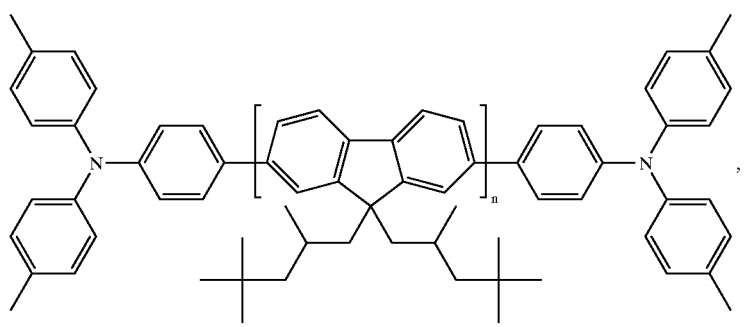,
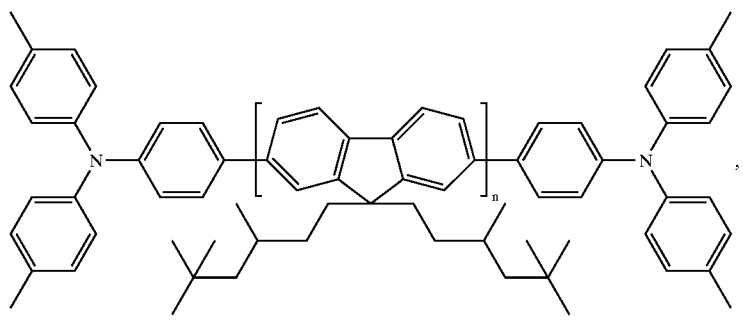,
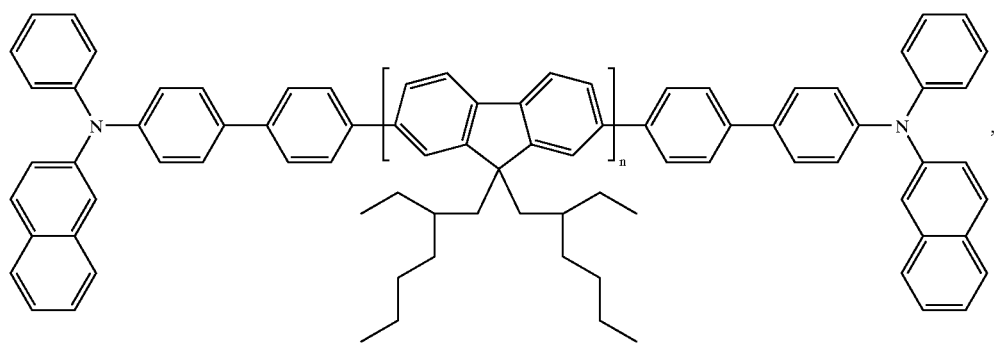,
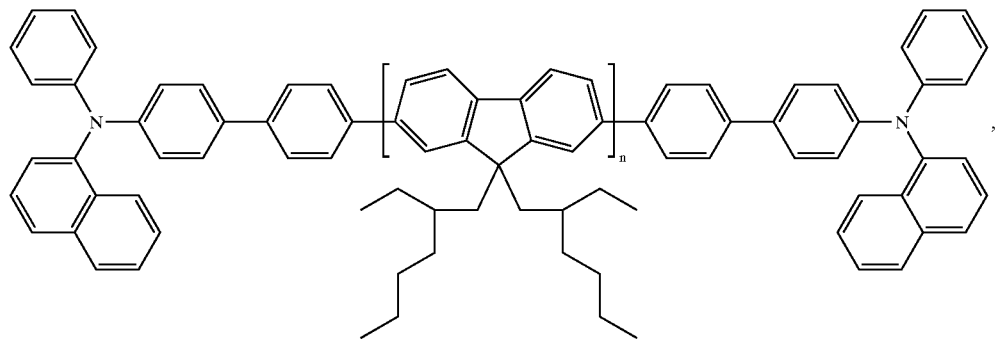,

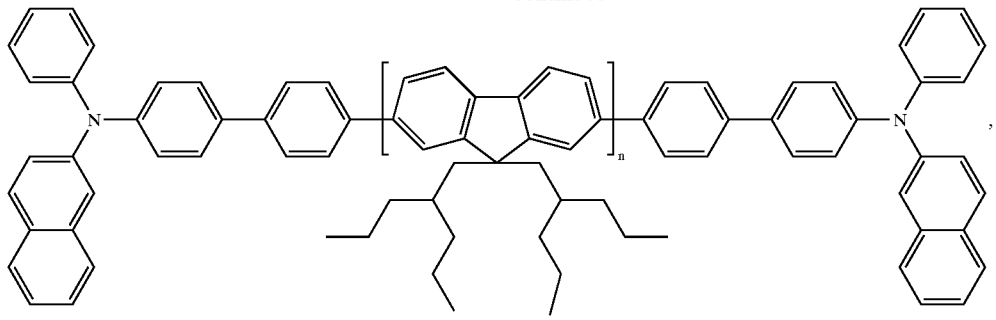

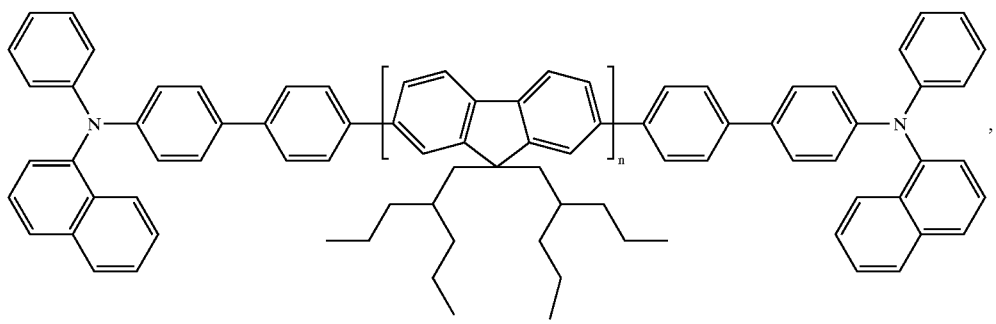

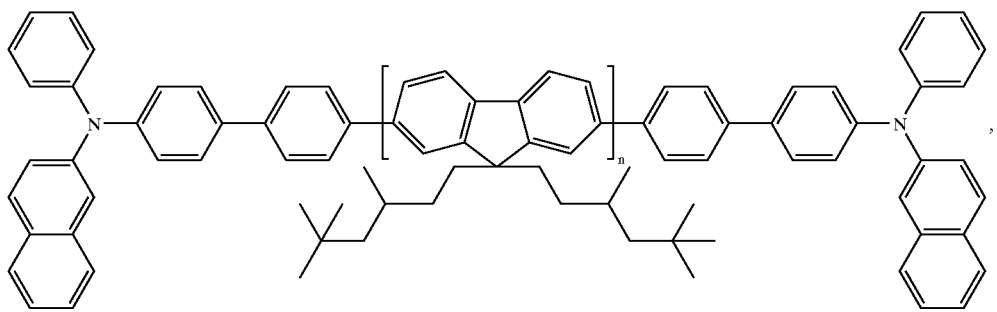

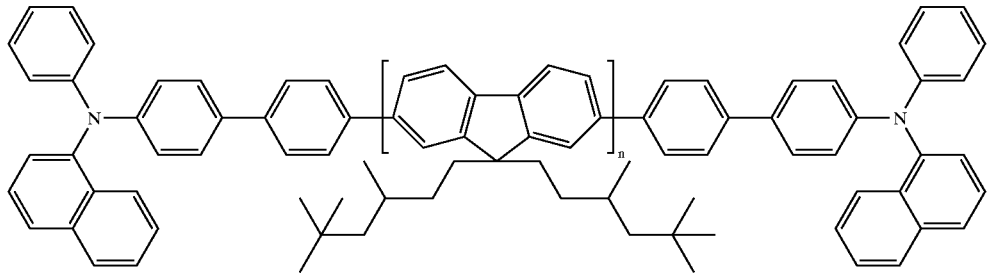

wherein n is as previously defined.

16. A film comprising a polyfluorene according to claim 1.

17. The film according to claim 16, wherein the film is aligned.

18. A film according to claim 16, further comprising at least one other substance selected from the group consisting of fluorescent dyes, hole-transporting moieties, electron-transporting moieties, ion-transporting moieties, phosphorescent dyes, nanoparticles, low, molecular weight liquid-crystalline moieties, other liquid-crystalline and/or fluorescent and/or phosphorescent and/or charge-transporting polymers.

19. The film according to claim 16, wherein the film is deposited on an alignment layer.

20. The film according to claim 16, wherein the film has a thickness ranging from 10 nm to 2 μm.

21. The device selected from the group consisting of FETs, photovoltaic elements, LEDs and sensors, incorporating a polyfluorene according to claim 1.

22. The device according to claim 21, further comprising another polymer.

23. The device according to claim 22, wherein said polymer is a luminescent polymer.

24. A device selected from the group consisting of FETs, photovoltaic elements, LEDs and sensors, further comprising a film according to claim 16.

25. A film comprising a polyfluorene according to claim 1.

26. The film according to claim 25, wherein the film is an emission layer.

27. A device selected from the group consisting of FETs, photovoltaic elements, LEDs and sensors, comprising a polyfluorene according to claim 1 and/or a film according to claim 16.

28. The device according to claim 24, further comprising a liquid-crystal display.

* * * * *

UNITED STATES PATENT AND TRADEMARK OFFICE
CERTIFICATE OF CORRECTION

PATENT NO. : 6,777,531 B2
DATED : August 17, 2004
INVENTOR(S) : Yasuda et al.

It is certified that error appears in the above-identified patent and that said Letters Patent is hereby corrected as shown below:

Title page,
Item [75], Inventors, should read:
-- Akio Yasuda, Stuttgart (DE);
  Wolfgang Knoll, Mainz (DE);
  Andreas Meisel, Frankfurt am Main (DE);
  Tzenka Miteva, Stuttgart (DE);
  Dieter Neher, Potsdam (DE);
  Heinz-Georg Nothofer, Stuttgart (DE);
  Ullrich Schrf, Golm (DE) --

Signed and Sealed this

Seventh Day of December, 2004

JON W. DUDAS
*Director of the United States Patent and Trademark Office*

UNITED STATES PATENT AND TRADEMARK OFFICE
CERTIFICATE OF CORRECTION

PATENT NO. : 6,777,531 B2  Page 1 of 1
DATED : August 17, 2004
INVENTOR(S) : Yasuda et al..

It is certified that error appears in the above-identified patent and that said Letters Patent is hereby corrected as shown below:

<u>Title page,</u>
Item [75], Inventor, should read
-- Akio Yasuda, Stuttgart (DE);
  Wolfgang Knoll, Mainz (DE);
  Andreas Meisel, Frankfurt am Main (DE);
  Tzenka Miteva, Stuttgart (DE);
  Dieter Neher, Potsdam (DE);
  Heinz-Georg Nothofer, Stuttgart (DE);
  Ullrich Scherf, Golm (DE) --

This certificate supersedes Certificate of Correction issued December 7, 2004.

Signed and Sealed this

Tenth Day of May, 2005

JON W. DUDAS
*Director of the United States Patent and Trademark Office*